United States Patent [19]
Kruse et al.

[11] Patent Number: 5,763,685
[45] Date of Patent: Jun. 9, 1998

[54] USE OF A SECOND STAGE REACTOR IN THE MANUFACTURE AND RECOVERY OF METHYL TERTIARY BUTYL ETHER

[75] Inventors: Charles Joseph Kruse, Cypress; Kyle Lee Preston, Port Arthur; Brian Lawrence Benac, Austin, all of Tex.

[73] Assignee: Huntsman Specialty Chemicals Corporation, Austin, Tex.

[21] Appl. No.: 516,227

[22] Filed: Aug. 17, 1995

[51] Int. Cl.$^6$ .................................................. C07C 41/00
[52] U.S. Cl. .......................... 568/698; 568/697; 568/699
[58] Field of Search ................................ 568/697, 698, 568/699

[56] References Cited

U.S. PATENT DOCUMENTS 5,243,091  9/1993  Kruse et al. ............................. 568/697

Primary Examiner—Marianne M. Cintins
Assistant Examiner—Dwayne C. Jones
Attorney, Agent, or Firm—Russell R. Stolle; Carl G. Ries

[57] ABSTRACT

MTBE is prepared from TBA and MeOH by passing a feed mixture comprising TBA and MeOH through a primary MTBE reaction zone to form a primary reaction product containing MTBE, unreacted TBA, unreacted MeOH, isobutylene and water; the primary reaction product is fractionated to provide a first lighter distillation fraction comprising isobutylene, MeOH and MTBE and a first higher boiling distillation fraction comprising MeOH, TBA and water and the first higher boiling distillation fraction is charged to a second stage MTBE reaction zone to form a second stage reaction product comprising unreacted MeOH, unreacted TBA water, isobutylene and MTBE.

8 Claims, 1 Drawing Sheet

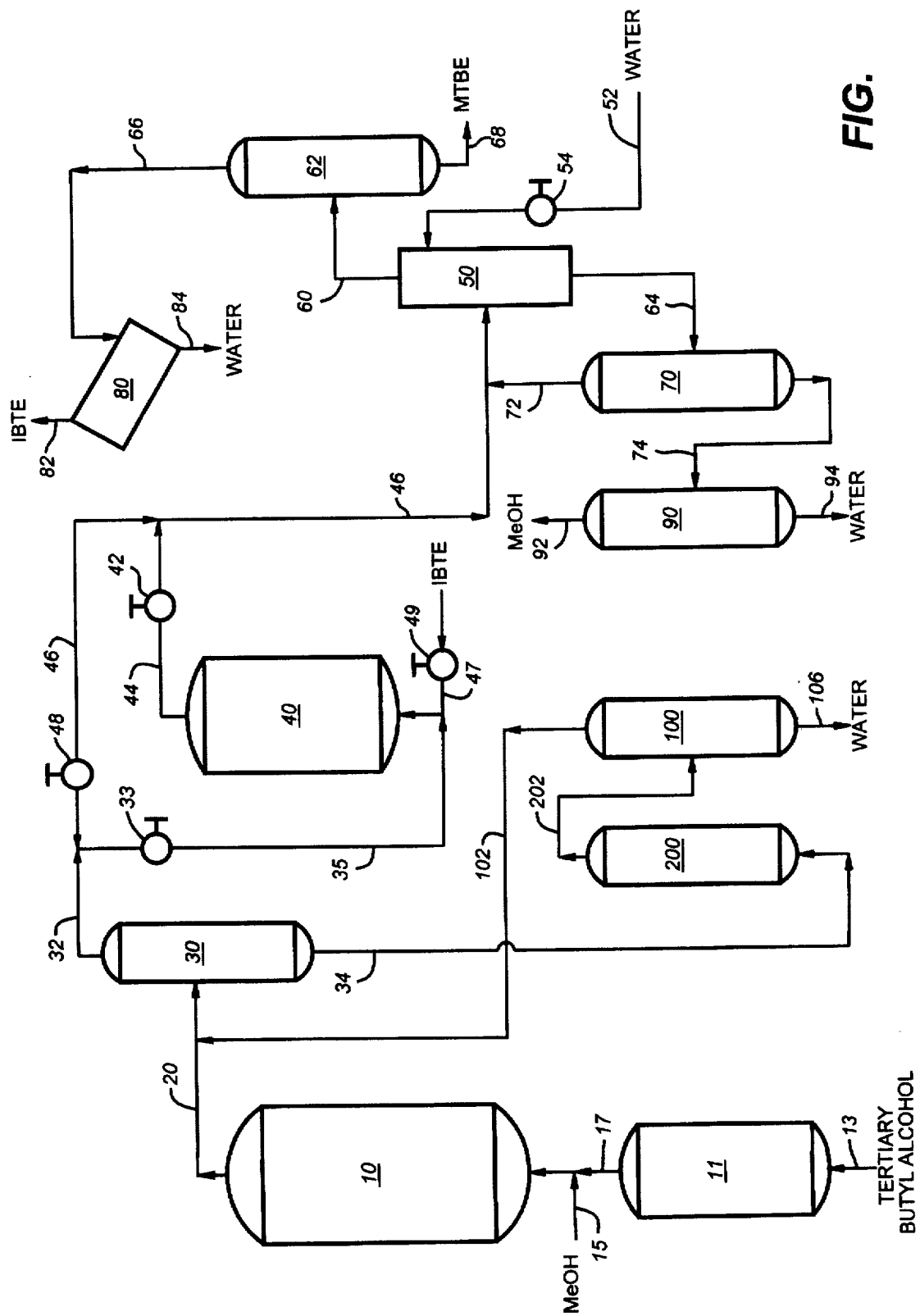

USE OF A SECOND STAGE REACTOR IN THE MANUFACTURE AND RECOVERY OF METHYL TERTIARY BUTYL ETHER

BACKGROUND OF THE INVENTION

1. Technical Field of the Invention

This invention relates to a method for the manufacture and purification of methyl tertiary butyl ether. More particularly, this invention relates to use of a second stage reactor in the manufacture of methyl tertiary butyl ether from tertiary butyl alcohol and methanol and to the purification of the methyl tertiary butyl ether formed by the reaction.

2. Prior Art

Kruse et al. U.S. Pat. No. 5,243,091 discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol, isobutylene and water, wherein the reaction product is separated in a distillation zone into a lighter fraction comprising methyl tertiary butyl ether, methanol, isobutylene and methyl tertiary butyl alcohol and a heavier fraction comprising tertiary butyl alcohol, methanol and water, and wherein the lighter fraction is charged to a finishing reactor wherein isobutylene and methanol are reacted to form additional methyl tertiary butyl ether.

Gupta U.S. Pat. No. 5,292,964 also discloses a process for the manufacture of methyl tertiary butyl ether from tertiary butyl alcohol and methanol wherein tertiary butyl alcohol is reacted with methanol in a primary reaction zone to provide a reaction product comprising methyl tertiary butyl ether, unreacted tertiary butyl alcohol, unreacted methanol and water, wherein the reaction product is separated in a distillation zone into a lighter fraction comprising substantially anhydrous methanol and methyl tertiary butyl alcohol and a heavier fraction comprising tertiary butyl alcohol, methanol and water, and wherein the lighter fraction is charged to a finishing reactor wherein the methanol is reacted with isobutylene to form additional methyl tertiary butyl ether.

In U.S. Pat. No. 4,144,138 (1979) to Rao et al. there is disclosed a method for recovering methyl tertiary butyl ether from an etherification reaction effluent by azeotropic distillation to recover a methanol-ether azeotrope overhead which is water-washed to give pure ether raffinate, the latter being azeotropically distilled to yield an ether-methanol overhead which is recycled to water washing.

The preparation of methyl tert-butyl ether from methanol and tert-butyl alcohol is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

Background Information

Methyl tert-butyl ether is finding increasing use as a blending component in high octane gasoline as the current gasoline additives based on lead and manganese are phased out. Current commercial processes for the manufacture of methyl tert-butyl ether are primarily based upon the liquid-phase reaction of isobutylene and methanol catalyzed by a cationic ion-exchange resin.

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have additional processes for making MTBE. It would be advantageous to have an efficient process for making MTBE by reaction of methanol with tertiary butyl alcohol, since t-butanol (TBA) is readily available commercially through isobutane oxidation.

It is known to react methanol with tertiary butyl alcohol in the presence of a catalyst in order to produce methyl tertiary butyl ether. A wide variety of catalysts have been suggested for this purpose.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

$$M_{2/n}O.Al_2O_3.xSiO_2.yH_2O$$

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungsto-phosphoric acid or 12-molybdophosphoric acid on an inert support, such as titania.

Two of the principal by-products formed during the reaction of the methanol with the tertiary butyl alcohol are water and isobutylene. Methanol and methyl tertiary butyl ether form an azeotrope which is broken only with difficulty and therefore the separation of methanol from MTBE during the recovery of purified methyl tertiary butyl ether presents a serious problem.

In U.S. Pat. No. 4,820,877, separation of methanol from MTBE is accomplished by using a refinery fuel gas to enhance the separation of methanol into the overhead stream of a distillation column.

In U.S. Pat. No. 4,814,517, separation of methanol from MTBE is accomplished by using a silica gel to preferentially adsorb methanol from an MTBE stream and by periodically regenerating the silica gel.

In U.S. Pat. No. 4,798,674, separation of methanol from MTBE is accomplished by using a membrane of cross-linked polyvinyl alcohol or a quaternary ammonium ion resin. Methanol preferentially permeates through the membrane increasing the MTBE concentration of the charge liquid.

In U.S. Pat. No. 4,759,850, separation of methanol from MTBE is accomplished by reverse osmosis.

In U.S. Pat. No. 4,440,963, separation of methanol from MTBE is accomplished by adding an agent such as 2-methyl pentane or Freon 113 to form an azeotrope with methanol. This azeotrope is recovered overhead giving a methanol-free MTBE bottoms product.

As recognized by Rao et al. in U.S. Pat. No. 4,144,138, isobutene (isobutylene) is formed as a by-product when methanol is reacted with tertiary butyl alcohol. In accordance with the Rao process, the isobutene is separated from the reaction product in an initial azeotropic distillation step as a noncondensable gas. Rao teach that part of the isobutene may be flashed from the reaction product for recycle, depending upon purity.

SUMMARY OF THE INVENTION

The present invention is directed to a method for the preparation of methyl tertiary butyl ether (MTBE) from tertiary butyl alcohol (TBA) and methanol (MeOH), which comprises the steps of:

a) continuously passing a feed mixture comprising tertiary butyl alcohol and methanol through a primary methyl tertiary butyl ether reaction zone containing a bed of a TBA/MeOH etherification catalyst under etherification reaction conditions to form a reaction product comprising methyl tertiary butyl ether, unreacted tertiary butyl alcohol, unreacted methanol, isobutylene and water, b) continuously charging the etherification reaction product to a methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, c) continuously charging said first higher boiling distillation fraction to second stage MTBE reaction zone containing a bed of a TBA/MeOH etherification catalyst and reacting the tertiary butyl alcohol and methanol therein to form a second stage etherification reaction product comprising unreacted methanol, unreacted tertiary butyl alcohol, water, isobutylene and methyl tertiary butyl ether.

DESCRIPTION OF PREFERRED EMBODIMENTS

I

The preferred embodiment of the present invention comprises a method for the continuous preparation of methyl tertiary butyl ether from tertiary butyl alcohol and methanol including the steps of:

a) continuously reacting a mixture of methanol and tertiary butyl alcohol in a primary MTBE reaction zone containing a bed of a TBA/MeOH etherification catalyst to form an etherification reaction product comprising unreacted methanol, unreacted tertiary butyl alcohol, water, isobutylene and methyl tertiary butyl ether, b) continuously charging the etherification reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, c) continuously charging the first heavier distillation fraction to a second stage MTBE reaction zone containing a bed of a TBA/MeOH etherification catalyst and reacting the tertiary butyl alcohol and methanol therein to form a second etherification reaction product comprising unreacted methanol, unreacted tertiary butyl alcohol, water, isobutylene and methyl tertiary butyl ether.

II

Another preferred embodiment of the present invention comprises a method for the continuous preparation of methyl tertiary butyl ether from tertiary butyl alcohol and methanol including:

a) continuously reacting a mixture of methanol and tertiary butyl alcohol in a primary MTBE reaction zone containing a bed of a TBA/MeOH etherification catalyst to form a primary etherification reaction product comprising unreacted methanol, unreacted tertiary butyl alcohol, water, isobutylene and methyl tertiary butyl ether, b) continuously charging the primary etherification reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, c) continuously charging the first higher boiling distillation fraction to second stage MTBE reaction zone containing a bed of a TBA/MeOH etherification catalyst and reacting the tertiary butyl alcohol and methanol therein to form a second stage etherification reaction product comprising unreacted methanol, unreacted tertiary butyl alcohol, water, isobutylene and methyl tertiary butyl ether, d) continuously charging the second stage reaction product to a second methyl tertiary butyl ether distillation zone and fractionating it therein to provide a second lower boiling distillation fraction comprising unreacted methanol, unreacted tertiary butyl alcohol, isobutylene and methyl tertiary butyl ether, and a second higher boiling distillation fraction comprising water, and e) recycling the second lower boiling distillation fraction to said first MTBE distillation zone.

III

When tertiary butyl alcohol is prepared from tertiary butyl hydroperoxide, the tertiary butyl alcohol reaction product will contain minor amounts of peroxide contaminants such as tertiary butyl hydroperoxide, ditertiary butyl peroxide, allyl tertiary butyl peroxide, etc. The peroxide contaminants tend to adversely affect catalyst performance. Also, when tertiary butyl alcohol contaminated with minor amounts of peroxides is reacted with methanol to form methyl tertiary butyl ether, the etherification reaction product resulting from the reaction will contain the peroxide contaminants.

In accordance with another embodiment of the present invention, a peroxides-contaminated tertiary butyl alcohol feedstock is passed through a peroxides decomposition reaction zone before being charged to the primary MTBE reaction zone so that the MTBE reaction product will be substantially free from peroxide contaminants.

In accordance with a further embodiment of the present invention, a modified process is provided wherein a peroxides-contaminated tertiary butyl alcohol feedstock is passed through a peroxides decomposition reaction zone to substantially completely decompose the peroxide contaminants contained therein, and then charged to a primary MTBE reaction zone together with methanol to form an isobutylene-containing methyl tertiary butyl ether etherification product that is substantially free from peroxide contaminants.

In accordance with this preferred embodiment of the present invention, a method for the continuous preparation of methyl tertiary butyl ether from tertiary butyl alcohol and methanol is provided comprising the steps of:

a) continuously charging a peroxides-contaminated tertiary butyl alcohol feedstock to a peroxides decomposition reaction zone and substantially completely decomposing the peroxide contaminants therein to form a substantially peroxides-free tertiary butyl alcohol product, b) continuously charging a reaction feed mixture comprising methanol and the substantially peroxides-free tertiary butyl alcohol product to a primary MTBE reaction zone containing a bed of a TBA/MeOH etherification catalyst and reacting the reaction feed mixture therein to form a primary etherification reaction product comprising unreacted methanol, unreacted tertiary butyl alcohol, water, isobutylene and methyl tertiary butyl ether, c) continuously charging the primary MTBE reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, d) continuously charging the first higher boiling distillation fraction to second stage MTBE reaction zone containing a bed of a TBA/MeOH etherification catalyst and partially reacting the tertiary butyl alcohol and methanol contained therein to form a second stage etherification reaction product comprising unreacted methanol, unreacted tertiary butyl alcohol, water, isobutylene and methyl tertiary butyl ether, e) continuously charging the second stage reaction product to a second methyl tertiary butyl ether distillation zone and fractionating it therein to provide a second lower boiling distillation fraction comprising unreacted methanol, unreacted tertiary butyl alcohol, isobutylene and methyl tertiary butyl ether, and a second higher boiling distillation fraction comprising water, and f) recycling the second lower boiling distillation fraction to said first methyl tertiary butyl ether distillation zone.

IV

In accordance with another embodiment of the present invention, a method for the continuous preparation of methyl tertiary butyl ether from tertiary butyl alcohol and methanol is provided comprising the steps of:

a) continuously charging a reaction feed mixture comprising methanol and substantially peroxides-free tertiary butyl alcohol to a primary MTBE reaction zone containing a bed of a TBA/MeOH etherification catalyst and reacting the reaction feed mixture therein to form a primary MTBE etherification reaction product comprising unreacted methanol, unreacted tertiary butyl alcohol, water, isobutylene and methyl tertiary butyl ether, b) continuously charging the primary MTBE reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, c) continuously charging the first higher boiling distillation fraction to second stage MTBE reaction zone containing a bed of a TBA/MeOH etherification catalyst and reacting the tertiary butyl alcohol and methanol therein to form a second stage etherification reaction product comprising unreacted methanol, unreacted tertiary butyl alcohol, water, isobutylene and methyl tertiary butyl ether, d) continuously charging the second stage reaction product to a second methyl tertiary butyl ether distillation zone and fractionating it therein to provide a second lower boiling distillation fraction comprising unreacted methanol, unreacted tertiary butyl alcohol, isobutylene and methyl tertiary butyl ether, and a second higher boiling distillation fraction comprising water, and e) recycling the second lower boiling distillation fraction to said first methyl tertiary butyl ether distillation zone, f) continuously charging an extraction feed comprising said first lower boiling distillation fraction, which contains isobutylene, methanol and methyl tertiary butyl ether to a methanol extraction zone and countercurrently contacting the extraction feed therein with water to provide an overhead extract comprising isobutylene, methyl tertiary butyl ether and a minor amount of water, and a raffinate comprising methanol, water and a minor amount of methyl tertiary butyl ether, g) continuously charging the extract to a third methyl tertiary butyl ether distillation zone and separating it therein into a third lower boiling distillation fraction comprising isobutylene and water and a third higher boiling distillation fraction consisting essentially of methyl tertiary butyl ether, h) continuously charging the raffinate from the methanol extraction zone to a fourth methyl tertiary butyl ether distillation zone and separating it therein into a fourth lower boiling distillation fraction comprising methyl tertiary butyl ether and a fourth higher boiling distillation fraction comprising water and methanol, i) continuously charging the fourth higher boiling distillation fraction to a fifth methanol distillation zone and separating it therein into a fifth lower boiling methanol fraction and a fifth higher boiling distillation fraction comprising water, and k) continuously charging the fifth lower boiling distillation fraction to the primary MTBE reaction zone.

V

In accordance with a further embodiment of the present invention, a method is provided for the continuous preparation of methyl tertiary butyl ether wherein the first lower boiling distillation fraction comprising isobutylene, methanol and methyl tertiary butyl ether is also processed in order to prepare and recover additional methyl tertiary butyl ether from isobutylene and methanol, the method comprising the steps of:

a) continuously charging a reaction feed mixture comprising methanol and substantially peroxides-free tertiary butyl alcohol to a primary MTBE reaction zone containing a bed of a TBA/MeOH etherification catalyst and reacting said reaction feed mixture therein to form a primary etherification reaction product comprising unreacted methanol, unreacted tertiary butyl alcohol, water, isobutylene and methyl tertiary butyl ether, b) continuously charging the primary reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, c) continuously charging the first higher boiling distillation fraction to second stage MTBE reaction zone containing a bed of a TBA/MeOH etherification catalyst and reacting the tertiary butyl alcohol and methanol therein to form a second stage etherification reaction product comprising unreacted methanol, unreacted tertiary butyl alcohol, water, isobutylene and methyl tertiary butyl ether, d) continuously charging the second stage reaction product to a second methyl tertiary butyl ether distillation zone and fractionating it therein to provide a second lower boiling distillation fraction comprising unreacted methanol, unreacted tertiary butyl alcohol, isobutylene and methyl tertiary butyl ether, and a second higher boiling distillation fraction comprising water, and e) recycling the second lower boiling distillation fraction to said first methyl tertiary butyl ether distillation zone f) continuously charging an isobutylene (IBTE) feedstock comprising the first lower boiling distillation fraction to a finishing reactor containing a solid resin IBTE/MeOH etherification catalyst and reacting the isobutylene and methanol contained therein to form a finishing reactor conversion product comprising MTBE, TBA, unreacted MeOH, unreacted IBTE and water, g) continuously charging the finishing reactor conversion product to a methanol extraction zone and countercurrently contacting the finishing reaction product therein with water to provide an overhead extract comprising isobutylene, methyl tertiary butyl ether and a minor amount of water, and a raffinate comprising methanol, water and a minor amount of methyl tertiary butyl ether, h) continuously charging the extract to a third methyl tertiary butyl ether distillation zone and separating it therein into a third lower boiling distillation fraction comprising isobutylene and water and a third higher boiling distillation fraction consisting essentially of methyl tertiary butyl ether, i) continuously charging the raffinate from the methanol extraction zone to a fourth methyl tertiary butyl ether distillation zone and separating it therein into a fourth lower boiling distillation fraction comprising methyl tertiary butyl ether and a fourth higher boiling distillation fraction comprising water and methanol, j) continuously charging the fourth higher boiling distillation fraction to a fifth methanol distillation zone and separating it therein into a fifth lower boiling methanol recycle fraction and a fifth higher boiling distillation fraction comprising water, and k) continuously charging the fifth lower boiling distillation fraction to the primary MTBE reaction zone.

DETAILED DESCRIPTION OF THE PRESENT INVENTION

The Etherification Reaction Catalyst

In accordance with the MTBE manufacture and purification method of the present invention, etherification reaction zones containing a bed of an etherification catalyst are utilized.

Any suitable solid resin etherification catalyst may be used, such as a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Peroxide Decomposition

When the tertiary butyl alcohol feedstock to be used in the preparation of methyl tertiary butyl ether is tertiary butyl alcohol contaminated with peroxides such as tertiary butyl hydroperoxide, ditertiary butyl peroxide, allyl tertiary butyl peroxide, etc., the feedstock is treated for the substantially complete removal of the peroxide contaminants before it is charged to the methyl tertiary butyl ether etherification zone.

It is known to prepare tertiary butyl alcohol by the thermal or catalytic decomposition of tertiary butyl hydroperoxide. It is also known to prepare tertiary butyl alcohol by the catalytic reaction of tertiary butyl hydroperoxide with propylene to form propylene oxide and tertiary butyl alcohol. The tertiary butyl alcohol feedstock derived from tertiary butyl hydroperoxide in this manner will contain peroxide contaminants. A typical feedstock prepared in this fashion will contain from about 95 to 99 wt. % of tertiary butyl alcohol and less than about 2.0 wt. % of peroxide contaminants.

In accordance with the present invention, the peroxides-contaminated tertiary butyl alcohol is charged to a peroxides decomposition reaction zone where the peroxides are substantially completely thermally and/or catalytically decomposed. The peroxide contaminants will be decomposed to form water and tertiary butyl alcohol, and trace amounts of other decomposition products such as acetone and methyl formate.

When the peroxides are to be thermally decomposed, the peroxides-contaminated tertiary butyl alcohol feedstock is continuously passed through a reactor in the peroxides decomposition reaction zone at a temperature of about 1000° to about 2000° C., a pressure of about 80 to about 500 psia at a flow rate of about 0.5 to 20 volumes of feedstock per reactor volume per hour to thereby provide a substantially peroxides-free tertiary butyl alcohol reaction product.

Alternately, the peroxide contaminants may be catalytically decomposed.

A wide variety of catalysts may be used for this purpose, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

The conversion conditions to be utilized in the peroxide decomposition zone may comprise, for example, a temperature of about 1000° to about 200° C., a pressure of about 80 to about 500 psia and a space velocity of about 0.5 to about 20 volumes of feed per volume of catalyst per hour.

The effluent from the peroxide decomposition zone will typically comprise about 95 to about 99 wt. % of tertiary butyl alcohol and less than about 0.1 wt. % of peroxide contaminants.

BRIEF DESCRIPTION OF THE DRAWING

The drawing is a schematic flow sheet which conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating a preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a primary MTBE reaction zone 10 containing a bed of solid etherification catalyst. Any suitably etherification catalyst may be used such as, for example, a solid resin etherification of the type described above, for example, a strongly acidic ion exchange resin consisting essentially of sulfonated polystyrene crosslinked with divinyl benzene (e.g., Dowex 50, Nalcite HCR, Amberlyst 15, etc.). As another example, the catalyst may be a fluorophosphoric acid-on-titania catalyst of the type disclosed in Knifton et al. U.S. Pat. No. 4,822,921 or a heteropoly acid such as 12-tungstophosphoric acid or 12-molybdophosphoric acid supported on an inert support such as titania.

When the tertiary butyl alcohol is prepared by the thermal or catalytic decomposition of tertiary butyl hydroperoxide, it will contain minor amounts of impurities such that, for example, the feedstock charged to the reaction zone 10 will contain the following components:

| ETHERIFICATION REACTION ZONE FEED MIXTURE | |
|---|---|
| Component | wt. % (approximate) |
| Methanol | 41.0 |
| TBA[1] | 47.0 |
| Acetone | 0.5 |
| 2-Propanol | 6.0 |
| MTBE[2] | 0.2 |
| DTBP[3] | 0.1 |
| t-Butyl Formate | 0.1 |
| Water | 6.0 |

[1]Tertiary butyl alcohol
[2]Methyl tertiary butyl ether
[3]Ditertiary butyl peroxide When the tertiary butyl alcohol feedstock to be initially charged to etherification reaction zone 10 is a peroxides-contaminated tertiary butyl alcohol feedstock, as described above, the tertiary butyl alcohol feedstock is initially charged by way of a tertiary butyl alcohol feed line 13 to a peroxides decomposition zone 11, operated, (e.g.) at a temperature of about 1000° to about 2000° C., a pressure of about 80 to about 500 psia and a flow rate of about 0.5 to 20 volumes of feedstock per reactor volume per hour to thereby provide a substantially peroxides-free tertiary butyl alcohol reaction product. The peroxide contaminants will be decomposed to form water and tertiary butyl alcohol, and trace amounts of other decomposition products such as acetone and methyl formate.

The substantially peroxides-free tertiary butyl alcohol reaction product is continuously discharged from the peroxides decomposition zone 11 by a discharge line 17 leading to the primary MTBE reaction zone 10. Fresh methanol is continuously charged to the line 17 by a line 15. The flow of methanol and tertiary butyl alcohol to the primary MTBE reaction zone 10 is regulated so that a molar excess of methanol is present in the line 17, such as, for example, a molar ratio of about 1.1 to about 3 moles of methanol per mol of tertiary butyl alcohol.

Within the primary MTBE reaction zone 10 the feed mixture is brought into contact with a bed of an etherification catalyst, such as a sulfonic acid resin etherification catalyst under reaction conditions including a pressure of about 30 to about 500 psia, and more preferably from about 200 to about 300 psia, a temperature of about 300° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed mixture per volume of etherification catalyst per hour are fed to the etherification reaction zone 10 and, more preferably from about 1 to about 4 volumes of feed mixture per volume of etherification catalyst per hour.

As a specific example, when the solid etherification catalyst is a sulfonic acid resin such as Amberlyst 15 and when the molar ratio of methanol to tertiary butyl alcohol in the feed mixture charged to the etherification reaction zone 10 by the line 17 is within the ratio of about 2.0 moles of methanol per mole of tertiary butyl alcohol, and the reaction is conducted at a temperature of about 100° C. at a feed rate of about 2.0 volumes of feed mixture per volume of catalyst per hour, a representative etherification reaction product may have the composition in part shown by the following table:

| ETHERIFICATION REACTION PRODUCT | |
|---|---|
| Component | % |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, ditertiary butyl peroxide, tertiary butyl formate, etc. initially present in the tertiary butyl alcohol feedstock.

The etherification reaction product is discharged from the primary MTBE reaction zone 10 by a line 20 leading to a first MTBE distillation zone 30 wherein it is fractionated under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation conditions being selected such that substantially all of the MTBE fed to the first MTBE distillation zone 30 by line 20 is taken overhead from the first distillation zone 30 by a line 32. As a consequence, the first lower boiling distillation fraction 32 taken overhead from the distillation zone 30 will comprise substantially all of the isobutylene and substantially all of the methyl tertiary butyl ether and some of the methanol charged to the first distillation zone 30. The first higher boiling distillation fraction 34 discharged from the first MTBE distillation zone 30 will comprise methanol, tertiary butyl alcohol and water. The first heavier distillation fraction will normally contain from about 30 to about 40 wt. % of methanol, from about 20 to about 30 wt. % of tertiary butyl alcohol, from about 35 to about 20 wt. % of water; oxygen-containing impurities comprising the balance.

The first higher boiling distillation fraction 34 is charged to second stage MTBE reaction zone 200 containing a bed of a TBA/MeOH etherification catalyst and the tertiary butyl alcohol and methanol contained therein are reacted to form a second stage etherification reaction product comprising unreacted methanol, unreacted tertiary butyl alcohol, water, isobutylene and methyl tertiary butyl ether.

Within the second stage methyl tertiary butyl ether etherification reaction zone 200 the feed is brought into contact with a bed of etherification catalyst, such as a sulfonic acid resin etherification catalyst under reaction conditions including a pressure of about 30 to about 500 psia, and more preferably from about 200 to about 300 psia, a temperature of about 300° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the etherification reaction zone is suitably such that about 0.5 to about 20 volumes of feed per volume of etherification catalyst per hour are fed to the etherification reaction zone 200 and, more preferably from about 1 to about 4 volumes of feed per volume of etherification catalyst per hour.

In accordance with the present invention the second methyl tertiary butyl ether etherification reaction product is discharged from the second stage methyl tertiary butyl ether etherification reaction zone 200 by a line 202 leading to a second distillation column 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, into a second lower boiling distillation fraction discharged by a line 102 and a second higher boiling distillation fraction comprising water, which is discharged by a line 106.

In accordance with the present invention the second lower boiling distillation fraction 102 is recycled to the line 20 leading to first MTBE distillation zone 30.

As noted above, the first lower boiling distillation fraction 32 taken overhead from the distillation zone 30 comprises substantially all of the isobutylene and substantially all of the methyl tertiary butyl ether and some of the methanol charged to the first distillation zone 30. The first lower boiling distillation fraction 32 is charged a via line 46 controlled by a valve 48 to a methanol solvent extraction zone 50 where it is countercurrently contacted with water introduced into the solvent extraction zone 50 by a charge line 52 controlled by a valve 54.

Within the methanol solvent extraction zone 50, solvent extraction conditions are established for countercurrent solvent extraction including a ratio of isobutylene to water within the range of about 0.8 to about 1.8 volumes of isobutylene per volume of water per hour, and more preferably a ratio of about 1.0 to about 1.5 volumes of isobutylene per volume of water per hour. Extractive conditions to be established may suitably include a temperature of about 20° to about 60° C., and more preferably from about 30° to about 40° C., and a pressure of about 50 to about 500 psia, and more preferably from about 50 to about 150 psia.

As a consequence, a supernatant extract will be formed which is withdrawn from the methanol solvent extraction zone 50 by line 60 leading to a third methyl tertiary butyl ether distillation zone 62. The raffinate is discharged from the solvent extraction zone 50 by way of a bottoms charge line 64 leading to a fourth methyl tertiary butyl ether distillation zone 70.

Within the third methyl tertiary butyl ether distillation zone 62, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a third lower boiling distillation fraction 66 discharged from the third distillation zone 62 and a third higher boiling distillation fraction 68 consisting essentially of product, namely methyl tertiary butyl ether.

The third lower boiling distillation fraction 66 will comprise a mixture of isobutylene and water and is suitably charged to a decantation zone 80 where it can settle to form a supernatant isobutylene phase withdrawn from the decantation zone 80 by way of a line 82. Water is discharged in the decantation zone 80 by way of a water discharge line 84 and is suitably purged from the system.

The raffinate 64 is charged to a fourth distillation column 70 and will comprise methyl tertiary butyl ether, methanol and water. It is fractionated in fourth distillation column 70 under distillation conditions including a liquid reflux temperature of about 30° to about 90° C., and more preferably from about 50° to about 75° C., and a reboiler temperature of about 80° to about 120° C., and more preferably from about 105° to about 115° C., and a pressure of about 15 to about 60 psia, and more preferably from about 40 to about 50 psia, to form a fourth lower boiling distillation fraction 72 comprising methyl tertiary butyl ether which suitably may be charged to the methanol solvent extraction zone 50. A fourth higher boiling distillation fraction comprising water and methanol is discharged from the fourth distillation zone 70 by a line 74 leading to a fifth distillation zone 90 where it is fractionated under distillation conditions that may suitably include a liquid reflux temperature of about 30° to about 80° C., and more preferably from about 60° to about 75° C., a reboiler temperature of about 100° to about 140° C., and more preferably from about 110° to about 120° C., and a pressure of about 15 to about 60 psia, and more preferably from about 20 to about 30 psia, into a fifth lower boiling distillation fraction 92.

A fifth higher boiling distillation fraction consisting essentially of water is discharged from the fifth methanol distillation zone by way of a line 94 and may be discharged from the system.

The first lower boiling distillation fraction 32 will normally contain from about 5 to about 10 wt. % of isobutylene, from about 70 to about 80 wt. % of methyl tertiary butyl ether and from about 10 to about 20 wt. % of methanol.

In accordance with one embodiment of the present invention, the valve 48 in the line 46 is closed and a valve 33 in a branch line 35 is opened so that the first lower boiling distillation fraction 32 may be brought into contact with a solid resin etherification catalyst in the finishing reactor 40 under conversion conditions including, for example, a temperature of about 35° to about 130° C., a pressure of about 30 to about 500 psia and a contact time of about 0.5 to about 20 volumes of first distillate fraction per volume of etherification catalyst per hour. As a consequence, a finishing reactor product is formed which will normally contain from about 0 to about 10 wt. % of isobutylene, about 75 to about 85 wt. % of methyl tertiary butyl ether and from about 10 to about 15 wt. % of methanol.

Etherification reaction conditions established in the finishing reactor 40 include, for example, a temperature of about 35° to about 130° C., and more preferably from about 40° to about 70° C., a pressure of about 50 to about 500 psia, and more preferably from about 150 to about 250 psia, and a contact time of about 0.5 to about 4 volumes of first distillation fraction per volume of solid resin etherification catalyst per hour. As a consequence, a portion of the methanol and isobutylene contained in the first distillation fraction 32 will be converted to methyl tertiary butyl ether. Typically, the conversion will amount to about 30 to about 60 wt. %, based on the isobutylene.

As a consequence, there will be formed an isobutylene conversion product discharged in the isobutylene conversion zone 40 by a line 42 leading to a methanol solvent extraction zone 50. The composition of a typical isobutylene conversion product may be characterized as follows:

| ISOBUTYLENE CONVERSION PRODUCT | |
|---|---|
| Component | wt. % |
| Isobutylene | 5.4 |
| MTBE | 79.5 |
| Methanol | 12.2 |
| Other | 2.9 |

The finishing reactor product is discharged from the finishing reactor 40 by a line 44 controlled by a valve 42 returning to the line 46 leading to the methanol extraction zone 50.

If desired, additional isobutylene may be charged to the line 35 leading to the finishing reactor 50, the additional isobutylene being added by a line 47 controlled by a valve 49.

EXAMPLES

The invention will be further illustrated by the following specific examples which are given by way of illustration, and not as a limitation on the scope of this invention. Where parts are mentioned, they are parts by weight.

In accordance with a preferred embodiment of the present invention, a tertiary butyl alcohol feedstock is continuously charged to peroxide decomposition zone 11 by a line 13 where it is thermally treated under thermal di-tertiary butyl peroxide decomposition conditions including a temperature of about 100° to about 200° C., a pressure of about 80 to about 500 psia and a flow rate of about 0.5 to 4 volumes of feedstock per reactor volume per hour to thereby provide a substantially peroxides-free tertiary butyl alcohol reaction product.

The peroxides-contaminated feedstock and the substantially peroxides-free reaction product discharged from the peroxide decomposition zone 11 will typically have compositions as follows:

| PEROXIDE DECOMPOSITION ZONE FEED AND PRODUCT | | |
|---|---|---|
| Component | Feed (wt. %) | Product (wt. %) |
| DTBP[1] | 0.87 | 0.02 |
| TBA[2] | 97.2 | 97.4 |
| Water | 0.1 | 0.02 |
| Other[3] | 1.8 | 2.6 |

[1]Ditertiary butyl peroxide
[2]Tertiary butyl alcohol
[3]Includes acetone, tertiary butyl formate, isopropyl alcohol, etc.

The feed mixture is charged by a line 17 leading to the primary MTBE reaction zone 10 containing a bed of a suitable etherification catalyst, such as Amberlyst 15 catalyst. Within the etherification reaction zone, the feedstock is passed through the etherification reaction bed on a continuous basis under reaction conditions, as described above, to thereby provide a reaction product having the following composition:

| ETHERIFICATION REACTION ZONE REACTION PRODUCT | |
|---|---|
| Component | wt. % (approx.) |
| Methanol | 2.8 |
| TBA | 14.5 |
| Water | 14.0 |
| Isobutylene | 3.0 |
| MTBE | 34.5 |
| Acetone | 0.4 |
| 2-Propanol | 6.0 |

The etherification zone reaction product is discharged from the reaction zone 10 by a line 20 leading to first methyl tertiary butyl ether distillation zone 30 where the fraction 20 is separated into first lower boiling distillation fraction 32 comprising about 6.5 wt. % isobutylene, about 16.5 wt. % methanol and about 75 wt. % MTBE and a first higher boiling fraction 34 comprising about 37 wt. % methanol, about 26.0 wt. % tertiary butyl alcohol, about 26 wt. % water, 11 wt. % isopropanol and about 0.5 wt. % of other components.

The first higher boiling distillation fraction 34 is charged to a second stage MTBE reaction zone 200. Within the second stage methyl tertiary butyl ether etherification reaction zone 200 the feed is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the second stage etherification reaction zone is suitably such that about 0.5 to about 20 volumes of feed per volume of etherification catalyst per hour are fed to the etherification reaction zone 200 and, more preferably from about 1 to about 4 volumes of feed per volume of etherification catalyst per hour.

By way of example, 25 cc of pre-soaked Amberlyst 15 catalyst were placed in an upflow reactor and a feed consisting of about 22.49 wt. % water, about 28.39 wt. % tertiary butyl alcohol, about 47.48 wt. % methanol, about 0.94 wt. % ditertiary butyl peroxide, and about 0.7 wt. % methyl tertiary butyl ether was charged to the reactor under reaction conditions including a temperature of about 110° C., 300 psi and a LHSV of 2. The results are summarized in the following table:

Amberlyst ® 15
110° C., LHSV 2, Second Stage Reactor Feed #1
Run 6617-73
Analysis of Reactor Effluent from MTBE Second Stage Reactor Test, 110° C., 300 psi, Amberlyst 15, LHSV 2, using Simulated Feed (22.5% H₂O, 0.74% MTBE, 28.4% TBA, 47.5% MeOH, and 0.96% DTBP)

| Hours | Sample # | TBA Conv. (%) | MTBE Select. (%) |
|---|---|---|---|
| 24 | 1 | 62.49 | 91.57 |
| 28 | 2 | 58.35 | 92.31 |

The TBA conversion and the MTBE selectivity were very good considering the amount of water present in the feed.

Next, a catalyst lifetime study was conducted using 25 cc of presoaked Amberlyst 16 catalyst in the upflow reactor using a feed composed of about 22.49 wt. % water, about 28.39 wt. % tertiary butyl alcohol, about 46.98 wt. % methanol, about 0.94 wt. % ditertiary butyl peroxide, about 0.5 wt. % allyl tertiary butyl peroxide and about 0.7 wt. % methyl tertiary butyl ether. The results are summarized in the following table.

Amberlyst ® 16
110° C. LHSV 2, Second Stage Reactor Feed #2
Run 6819-2
Analysis of Reactor Effluent from MTBE Second Stage
Reactor Test, 120° C., 300 psi, Amberlyst 16, LHSV 2,
using Simulated Feed (22.5% H₂O, 0.74% MTBE, 28.4%
TBA, 47.5% MeOH, 0.96% DTBP and 0.5% ATBP)

| Sample # | Hours | TBA Conv. % | MTBE Select. % | % Decom DTBP | % Decom ATBP | DME in Sample (ppm) |
|---|---|---|---|---|---|---|
| 1 | 20 | 62.48 | 90.09 | 13.0 | 69.6 | 1970 |
| 2 | 88 | 59.34 | 91.42 | 22.8 | 82.7 | 1800 |
| 3 | 136 | 59.74 | 90.86 | 19.3 | 88.4 | 1730 |
| 4 | 184 | 59.19 | 90.65 | 20.3 | 90.0 | 1640 |
| 5 | 256 | 59.71 | 90.24 | 15.5 | 89.1 | 1400 |
| 6 | 304 | 59.87 | 90.58 | 31.6 | 93.0 | 1860 |
| 7 | 376 | 58.16 | 91.75 | 20.5 | 95.4 | 1690 |
| 8 | 424 | 57.50 | 91.98 | 41.3 | 94.9 | 1720 |
| 9 | 448 | 56.96 | 91.97 | 45.9 | 97.5 | 1760 |
| 10 | 472 | 58.50 | 92.09 | 38.8 | 97.2 | 1560 |
| Avg. | | 59.1 | 91.2 | 26.9 | 89.8 | 1713 |

During the study, TBA conversion averaged about 59.1% and the MTBE selectivity was 92.1%. On average, about 27% of the ditertiary butyl peroxide decomposed and about 90% of the allyl tertiary butyl peroxide decomposed. About 1710 ppm of dimethyl ether (DME) formed. The reason for the large amount of DME in the reactor effluent can be attributed to the large amount of methanol relative to the TBA in the feed.

In accordance with the present invention the second methyl tertiary butyl ether etherification reaction product is discharged from the second stage methyl tertiary butyl ether etherification reaction zone 200 by a line 202 leading to a second distillation column 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, into a second lower boiling distillation fraction discharged by a line 102 and a second higher boiling distillation fraction comprising water, which is discharged by a line 106.

In accordance with the present invention the second lower boiling distillation fraction 102 is recycled to the line 20 leading to first MTBE distillation zone 30.

In accordance with one embodiment of the present invention, the first lower boiling distillation fraction 32 is continuously charged to a finishing reactor 40 through branch line 35 and brought into contact therein with a solid resin etherification catalyst, such as Amberlyst 15 catalyst, under conversion conditions, as described above, to thereby convert about 50 wt. % of the isobutylene and a portion of the methanol in the first distillation fraction to MTBE and to form a finishing reactor product which is discharged from the finishing reactor 40 by a line 44 and which typically has the following composition:

ISOBUTYLENE CONVERSION FEED AND PRODUCT, wt. %

| Component | Feed | Product |
|---|---|---|
| Isobutylene | 11 | 5.5 |
| MTBE | 71 | 80 |
| Methanol | 15 | 12 |
| Other | 3 | 3 |

The finishing reactor product 44 is continuously charged by a line 46 leading to methanol extraction zone 50. Water is charged to the methanol extraction zone 50 by a water charge line 52 in an amount such that the ratio of water to isobutylene in the methanol extraction zone 50 is in the range of about 0.1 to about 0.3 parts of water per part of isobutylene.

Within the methanol extraction zone, the methanol is extracted from the isobutylene conversion product under extraction conditions as described above to thereby provide an overhead (extract) fraction 60 comprising isobutylene and methyl tertiary butyl ether and a raffinate 64 comprising MTBE, methanol and water.

The extract is fed by a line 60 to a third methyl tertiary butyl ether purification distillation zone 62 where it is resolved by distillation into a third lower boiling distillation fraction 66 comprising isobutylene and water and into a third higher boiling distillation fraction 68 consisting essentially of methyl tertiary butyl ether which is discharged as product.

The third distillation fraction 66 is charged to a decantation separation zone 80 where it is permitted to settle and is resolved into an isobutylene fraction 82 and a water fraction 84 which is discharged from the system.

The isobutylene fraction 82 can be discharged from the system or recycled to the finishing reactor 40 in admixture with the first distillation fraction 32.

Typically, about 2 to about 5 parts of recycle isobutylene from the line 89 will be mixed with 100 parts of overhead product from the first distillation fraction 32.

The raffinate 64 is continuously charged to a fourth methyl tertiary butyl ether distillation zone 70 where it is separated into a fourth lower boiling distillation fraction 72 comprising methyl tertiary butyl ether and a fourth higher boiling distillation fraction 74 comprising methanol and water. The fraction 74 is continuously charged to a fifth methanol distillation zone 90 wherein it is separated by fractional distillation into a fifth lower boiling distillation fraction 92 comprising methanol and a fifth higher boiling distillation fraction comprising water which is discharged by a line 94.

Having thus described our invention, what is claimed is:

1. A method for the continuous preparation of methyl tertiary butyl ether (MTBE) from tertiary butyl alcohol (TBA) and methanol (MeOH), which comprises the steps of:

a) continuously reacting a mixture of methanol and tertiary butyl alcohol in a primary MTBE reaction zone containing a bed of a TBA/MeOH etherification catalyst to form a primary etherification reaction product comprising unreacted methanol, unreacted tertiary butyl alcohol, water, isobutylene and methyl tertiary butyl ether, b) continuously charging the primary etherification reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, c) continuously charging the first higher boiling distillation fraction to second stage MTBE reaction zone containing a bed of a TBA/MeOH etherification catalyst and reacting the tertiary butyl alcohol and methanol therein to form a second stage etherification reaction product comprising unreacted methanol, unreacted tertiary butyl alcohol, water, isobutylene and methyl tertiary butyl ether, d) continuously charging the second stage reaction product to a second methyl tertiary butyl ether distillation zone and fractionating it therein to provide a second lower boiling distillation fraction comprising unreacted methanol, unreacted tertiary butyl alcohol, isobutylene and methyl tertiary butyl ether, and a second higher boiling distillation fraction comprising water, and e) recycling said second lower boiling distillation fraction to said first MTBE distillation zone.

2. A method as in claim 1 wherein the TBA/MeOH etherification catalyst is a solid resin divinyl benzene cross-linked sulfonated polystyrene catalysts, wherein methanol is reacted with the tertiary butyl alcohol in the primary MTBE reaction zone and the second stage MTBE reaction zone at a temperature of about 90° C. to about 140° C. and a pressure of about 30 to 500 psia at a flow rate of about 0.5 to 20 volumes of feed mixture per volume of etherification catalyst per hour and wherein the methanol and tertiary butyl alcohol are charged to the primary MTBE reaction zone in the molar ratio of about 1.1 to about 3.0 moles of methanol per mole of tertiary butyl alcohol.

3. A method as in claim 1 including the additional steps of:

f) countercurrently contacting the first lighter distillation fraction with water in a methanol extraction zone in the ratio of about 0.8 to about 1.8 volumes of extraction feed mixture per volume of water at a temperature of about 20° to about 60° C. and a pressure of about 50 to 500 psia, to provide an overhead extract comprising isobutylene, methyl tertiary butyl ether and a minor amount of water, and a raffinate comprising methanol, water and a minor amount of methyl tertiary butyl ether, g) continuously charging the extract to a third methyl tertiary butyl ether distillation zone and separating it therein into a third lighter distillation fraction comprising isobutylene and water and a third heavier distillation fraction consisting essentially of methyl tertiary butyl ether, h) continuously charging the third lighter distillation fraction to a decantation separation zone and separating it therein into an isobutylene fraction and a water fraction.

4. A method for the continuous preparation of methyl tertiary butyl ether (MTBE) from tertiary butyl alcohol (TBA) and methanol (MeOH), which comprises the steps of:

a) continuously charging a peroxides-contaminated tertiary butyl alcohol feedstock to a peroxides decomposition reaction zone and substantially completely decomposing the peroxide contaminants therein to form a substantially peroxides-free tertiary butyl alcohol product, b) continuously charging a reaction feed mixture comprising methanol and the substantially peroxides-free tertiary butyl alcohol product to a primary MTBE reaction zone containing a bed of a TBA/MeOH etherification catalyst and reacting said reaction feed mixture therein to form a primary etherification reaction product comprising unreacted methanol, unreacted tertiary butyl alcohol, water, isobutylene and methyl tertiary butyl ether, c) continuously charging the primary MTBE reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, d) continuously charging said first higher boiling distillation fraction to second stage MTBE reaction zone containing a bed of a TBA/MeOH etherification catalyst and partially reacting the tertiary butyl alcohol and methanol contained therein to form a second stage etherification reaction product comprising unreacted methanol, unreacted tertiary butyl alcohol, water, isobutylene and methyl tertiary butyl ether, e) continuously charging the second stage reaction product to a second methyl tertiary butyl ether distillation zone and fractionating it therein to provide a second lower boiling distillation fraction comprising unreacted methanol, unreacted tertiary butyl alcohol, isobutylene and methyl tertiary butyl ether, and a second higher boiling distillation fraction comprising water, and f) recycling said second lower boiling distillation fraction to said first methyl tertiary butyl ether distillation zone.

5. A method for the continuous preparation of methyl tertiary butyl ether (MTBE) from tertiary butyl alcohol (TBA) and methanol (MeOH), which comprises the steps of:

a) continuously charging a reaction feed mixture comprising methanol and substantially peroxides-free tertiary butyl alcohol to a primary MTBE reaction zone containing a bed of a TBA/MeOH etherification catalyst and reacting said reaction feed mixture therein to form a primary etherification reaction product comprising unreacted methanol, unreacted tertiary butyl alcohol, water, isobutylene and methyl tertiary butyl ether, b) continuously charging the primary reaction product to a first methyl tertiary butyl ether distillation zone and separating it therein into a first lower boiling distillation fraction comprising isobutylene, methanol and methyl tertiary butyl ether and a first higher boiling distillation fraction comprising methanol, tertiary butyl alcohol and water, c) continuously charging said first higher boiling distillation fraction to second stage MTBE reaction zone containing a bed of a TBA/MeOH etherification catalyst and reacting the tertiary butyl alcohol and methanol therein to form a second stage etherification reaction product comprising unreacted methanol, unreacted tertiary butyl alcohol, water, isobutylene and methyl tertiary butyl ether, d) continuously charging the second stage reaction product to a second methyl tertiary butyl ether distillation zone and fractionating it therein to provide a second lower boiling distillation fraction comprising unreacted methanol, unreacted tertiary butyl alcohol, isobutylene and methyl tertiary butyl ether, and a second higher boiling distillation fraction comprising water, and e) recycling said second lower boiling distillation fraction to said first methyl tertiary butyl ether distillation zone.

f) continuously charging an isobutylene (IBTE) feedstock comprising the first distillation fraction to a finishing reactor containing a solid resin IBTE/MeOH etherification catalyst and reacting the isobutylene and methanol contained therein to form a finishing reactor conversion product comprising MTBE, TBA, unreacted MeOH, unreacted IBTE and water, g) continuously charging said finishing reactor conversion product to a methanol extraction zone and countercurrently contacting the finishing reaction product therein with water to provide an overhead extract comprising isobutylene, methyl tertiary butyl ether and a minor amount of water, and a raffinate comprising methanol, water and a minor amount of methyl tertiary butyl ether, h) continuously charging the extract to a third methyl tertiary butyl ether distillation zone and separating it therein into a third lower boiling distillation fraction comprising isobutylene and water and a third higher boiling distillation fraction consisting essentially of methyl tertiary butyl ether, i) continuously charging the raffinate from the methanol extraction zone to a fourth methyl tertiary butyl ether distillation zone and separating it therein into a fourth lower boiling distillation fraction comprising methyl tertiary butyl ether and a fourth higher boiling distillation fraction comprising water and methanol, j) continuously charging the fourth heavier distillation fraction to a fifth methanol distillation zone and separating it therein into a fifth lower boiling methanol recycle fraction and a fifth higher boiling distillation fraction comprising water, and k) continuously charging the fifth lower boiling distillation fraction to the primary MTBE reaction zone.

6. A method as in claim 5 wherein the TBA/MeOH etherification catalyst is a solid resin divinyl benzene crosslinked sulfonated polystyrene catalysts, wherein methanol is reacted with the tertiary butyl alcohol in the primary MTBE reaction zone and the second stage MTBE reaction zone at a temperature of about 90° C. to about 140° C. and a pressure of about 30 to 500 psia at a flow rate of about 0.5 to 20 volumes of feed mixture per volume of etherification catalyst per hour and wherein the methanol and tertiary butyl alcohol are charged to the primary MTBE reaction zone in the molar ratio of about 1.1 to about 3.0 moles of methanol per mole of tertiary butyl alcohol.

7. A method as in claim 6 wherein the IBTE/MeOH etherification catalyst is a solid resin divinyl benzene crosslinked sulfonated polystyrene catalyst, and wherein the isobutylene reaction mixture is reacted in the finishing reactor at a temperature of about 35° to about 130° C., a pressure of about 50 to 500 psia and a flow rate of about 0.5 to about 4 volumes of reaction mixture per volume of catalyst per hour.

8. A method as in claim 5 including the additional steps of:

l) continuously charging the raffinate from the methanol extraction zone to a third methyl tertiary butyl ether distillation zone and separating it therein into a lower boiling fifth distillation fraction comprising methyl tertiary butyl ether and a higher boiling sixth distillation fraction comprising water and methanol, m) continuously charging the sixth distillation fraction to a fourth methanol distillation zone and separating it therein into a seventh lower boiling recycle fraction and an eighth higher boiling distillation fraction, n) continuously charging the second heavier distillation fraction to a fifth distillation zone and separating it therein into a ninth lower boiling distillation recycle fraction comprising methanol and tertiary butyl alcohol, and a higher boiling tenth distillation fraction, o) continuously charging the fifth lower boiling distillation fraction to the methanol extraction zone, and p) continuously charging the seventh distillation fraction and the ninth distillation fractions to the methyl tertiary butyl ether etherification reaction zone.

* * * * *